(12) United States Patent
Krispi

(10) Patent No.: US 8,568,338 B2
(45) Date of Patent: Oct. 29, 2013

(54) DEVICE FOR IMPROVED EXTERNAL FETAL MONITORING

(76) Inventor: Jennifer Krispi, Santa Barbara, CA (US)

( * ) Notice: Subject to any disclaimer, the term of this patent is extended or adjusted under 35 U.S.C. 154(b) by 449 days.

(21) Appl. No.: 12/694,176

(22) Filed: Jan. 26, 2010

(65) Prior Publication Data

US 2010/0292576 A1  Nov. 18, 2010

Related U.S. Application Data

(60) Provisional application No. 61/179,204, filed on May 18, 2009, provisional application No. 61/181,221, filed on May 26, 2009.

(51) Int. Cl.
*A61B 5/103* (2006.01)

(52) U.S. Cl.
USPC ........................................ 600/591

(58) Field of Classification Search
USPC .................... 600/586–588, 595; 73/654, 658; 607/902
See application file for complete search history.

(56) References Cited

U.S. PATENT DOCUMENTS

| 4,401,125 | A |   | 8/1983  | Taylor et al. |         |
|-----------|---|---|---------|---------------|---------|
| 4,763,660 | A |   | 8/1988  | Kroll et al.  |         |
| 4,867,265 | A |   | 9/1989  | Wright        |         |
| 5,168,876 | A |   | 12/1992 | Quedens et al.|         |
| 5,701,917 | A |   | 12/1997 | Khouri        |         |
| 6,151,520 | A |   | 11/2000 | Combs         |         |
| 6,551,425 | B2|   | 4/2003  | Sylvester     |         |
| 6,749,573 | B2|   | 6/2004  | Bryant et al. |         |
| 7,340,287 | B2| * | 3/2008  | Mason et al.  | 600/344 |
| 2003/0187370 | A1 | * | 10/2003 | Kodama    | 600/591 |
| 2005/0215901 | A1 |   | 9/2005  | Anderson et al. |     |
| 2010/0191154 | A1 | * | 7/2010  | Berger et al. | 600/595 |

FOREIGN PATENT DOCUMENTS

WO  WO2007099309 A1  9/2007

* cited by examiner

*Primary Examiner* — Elmer Chao
(74) *Attorney, Agent, or Firm* — Trojan Law Offices

(57) ABSTRACT

The present invention described herein is a soft, pliable, cushioning device to be used in conjunction with ultrasound and toco transducers during external fetal monitoring. The device can be shaped to fit the transducers and can easily attach and detach with the transducers via an adhesive layer. The device provides comfort to the patient and improved continuity of the transducers' readings during external fetal monitoring. The device can be a single-use application or reusable.

8 Claims, 6 Drawing Sheets

US 8,568,338 B2

DEVICE FOR IMPROVED EXTERNAL FETAL MONITORING

CROSS-REFERENCE TO RELATED APPLICATIONS

This application claims priority to U.S. Provisional Application Ser. No. 61/179,204, filed on May 18, 2009, and U.S. Provisional Application Ser. No. 61/181,221, filed on May 26, 2009.

FIELD OF THE INVENTION

The present invention relates to a device to be used during external fetal monitoring to provide improved comfort and obtain more continuous readings during external fetal monitoring.

BACKGROUND OF THE INVENTION

Cardiotocography is a means of recording the fetal heartbeat and uterine contractions during pregnancy. Physicians have used this method, also known as external fetal monitoring, since the late 1970's. Two separate transducers perform simultaneous recordings of fetal heart rate and uterine contractions when placed externally on a woman's abdominal wall. In particular, an ultrasound transducer measures the fetal heart and a pressure-sensitive contraction transducer, also known as a tocodynamometer (toco), measures the tension of the maternal abdominal wall, which is an indirect measure of the intrauterine pressure. Both the ultrasound and toco transducers can be kept in place on the woman's abdomen with either a belt or a band.

Women can be monitored for days and or weeks depending on their risk needs. Women in labor are also monitored at the very least for approximately 20-40 minutes upon arrival to a hospital and then throughout the course of their labor. The time women are monitored can vary depending on their needs in labor as assessed by the provider. Despite the often extensive duration of external fetal monitoring, the external fetal monitoring equipment is heavy and inflexible. The equipment is also ridged and often leaves indentations on the woman's body. It is also challenging to trace the fetal heart rate using the equipment because the fetus will often move during monitoring and it can be time consuming to constantly adjust the transducers and belts during labor and birth. Moreover, patients often take off the transducers because of their discomfort. The transducers can also slide and lose position and therefore result in discontinuous readings during external fetal monitoring. While the readout device used with the fetal monitoring equipment has been modified to display information about multiple fetuses, the woman's blood pressure, and various other vital statistics, the design of the toco and ultrasound transducers have not changed since the introduction of external fetal monitoring.

Therefore, what is needed in the art is a product that can provide more comfortable and improved external fetal monitoring. In addition, the product should reduce the time and effort expended by the provider during external fetal monitoring. With these goals in mind, the inventor has created padded, pliable device to be used with the ultrasound and toco transducers to improve comfort during external fetal monitoring and allow for easy and continuous tracing of the fetal heart rate. The inventor has also created a device to maintain the positions of the transducers during external fetal monitoring. By maintaining the position of the transducers, the device also stabilizes the transducers to allow for improved, more comprehensive, continuous, and uninterrupted ultrasound and toco transducer readings during external fetal monitoring.

SUMMARY OF THE INVENTION

The present invention describes a device for use with a transducer during external fetal monitoring. The device is comprised of at least one layer comprised of a cushioning material that has an aperture therethrough and an exterior edge. The device also has an adhesive layer attached with the layer of cushioning material, wherein the adhesive layer removably attaches with a transducer. External fetal monitoring is accomplished with greater comfort for a woman when the device is attached with the transducer during external fetal monitoring. The device also allows for continuous transducer readings during external fetal monitoring.

The device can further comprise a cutout portion comprised of said cushioning material, wherein the cutout portion is equal to or less than the size of the aperture of the device. The cutout portion includes an adhesive layer that removably attaches with a transducer.

The exterior edge of the device can include at least one notch therethrough so that the device can fold over the transducer's edge. The cushioning material of the device can be any material that is capable of providing comfort and is non-irritating to a patient's skin, including, but not limited to, a polyester, a polyether and a polyurethane material.

An external fetal monitoring system is also described, wherein the system comprises a transducer and the aforementioned device. The transducer has at least one sensor element to measure fetal heart rate or intrauterine pressure and has an insulating layer to protect the patient from shock. External fetal monitoring is accomplished with greater comfort for a woman when the device is attached with the transducer during external fetal monitoring. The device also allows for continuous transducer readings during external fetal monitoring.

The external fetal monitoring system can also be described as a system for use with a patient for monitoring a fetus. The system includes a transducer which has a ring having an interior circumference and an exterior edge, at least one sensor element to detect fetal heart rate or intrauterine pressure, and an insulating layer shielding the patient from electrical shock located at least partially within the interior circumference of the ring. The system also includes at least one cushioning layer distributed about said exterior edge of said ring. The monitoring of the fetus is accomplished with greater continuity and greater comfort for a woman using the system described herein.

DETAILED DESCRIPTION OF THE INVENTION

Figure 1A:
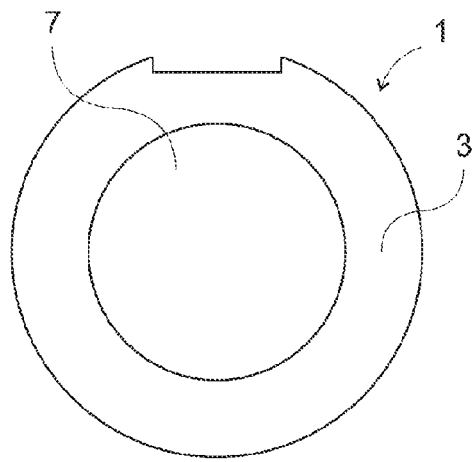
FIG. 1A is a top orthogonal view of a device according to the present invention.

The present invention overcomes disadvantages of the prior art, as identified and disclosed by the inventor, by providing an easy-to-use device to be used in conjunction with ultrasound transducers and toco transducers to improve comfort for a patient and improve the continuity of the transducer readings of the transducers during external fetal monitoring. Ultrasound and toco transducers are used externally on a patient's abdomen during external fetal monitoring. Ultrasound transducers measure the fetal heart and toco transducers measure the tension of the maternal abdominal wall, which is an indirect measure of the intrauterine pressure. The transducers known in the art include insulation to protect the patient from electric shock but do not disclose any means for providing comfort to the patients or maintaining the position of the transducers during external fetal monitoring. Rather, the transducers are formed in hard plastic shells. The absence of any cushioning can present problems for the practitioner during fetal heart monitoring, as the patient can often disrupt the monitoring and move the transducers due to the discomfort of the transducers. Further, the transducer can slip and move due to the absence of a cushioned, textured layer and result in inaccurate and discontinuous transducer readings.

Top and bottom orthogonal views of the device are illustrated in FIGS. 1A-1D. The device 1 described herein is an additional and separate external layer that attaches with the transducers to provide comfort to the patient, enable easier manipulation of the transducers for the practitioner, and maintain the position of the transducers. The device 1 overlays the hard ultrasound or toco transducers known in the art to provide greater comfort for a woman during external fetal monitoring in various stages of gestation, including labor, birth, and the antenatal period. The device 1 also enables the user to perform a more continuous and easier trace of a moving fetus during monitoring because the flexible device 1 can bend to conform to the woman's curved body and covers more surface area of the woman's body during monitoring compared to a transducer used by itself.

The device 1 is comprised of at least one layer of a cushioning material 3 that is attached with an ultrasound transducer or a toco transducer via an adhesive layer 4. The device 1 can be formed in any shape so long as the device 1 can sufficiently attach with the transducer. The device 1 can be made using die cutting tools. The cushioning material of the device 1 can be latex-free and comprised of any non-irritating material, including, but not limited to polyester, polyether and/or polyurethane foam material, such as goggle foam. The cushioning material can be comprised of silicone, rubber, or any other material known in the art that will provide a cushioning effect and not irritate the skin of the patient. The device 1 can be comprised of a single layer of cushioning material or multiple layers of different cushioning materials. The device can also include an aperture 7 through its center, to help retain the ultrasonic gel used with the transducers and to allow for a clear trace of the fetal heart rate or contractions without the device 1 obstructing the transducers' ability to measure the fetal heart or the tension of the maternal abdominal wall readings.

Figure 1B:
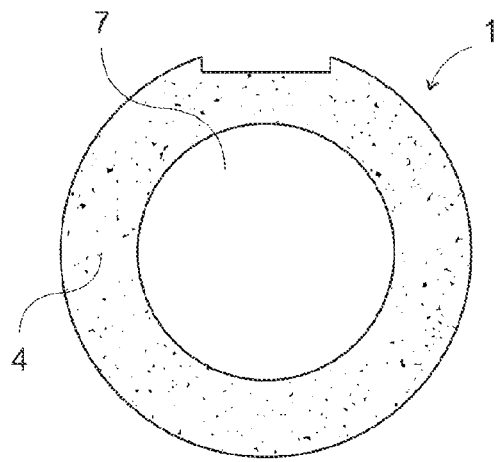
FIG. 1B is a bottom orthogonal view of a device according to the present invention.
Figure 1C:
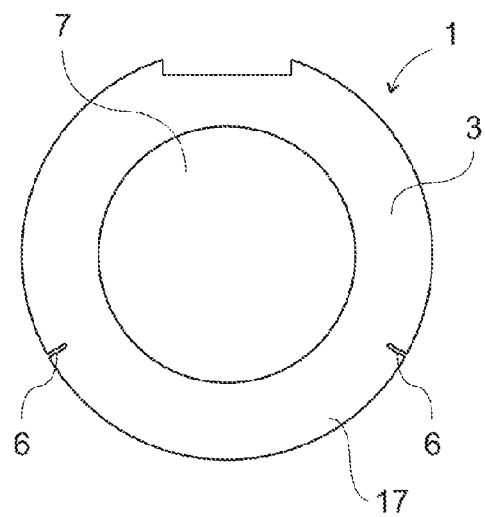
FIG. 1C is a top orthogonal view of a device according to the present invention.
Figure 1D:
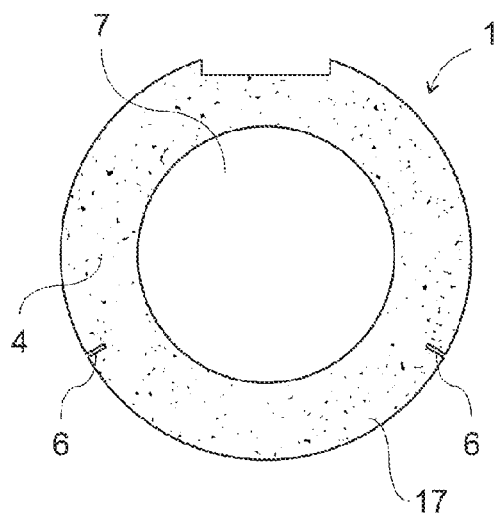
FIG. 1D is a bottom orthogonal view of a device according to the present invention.
Figure 2:
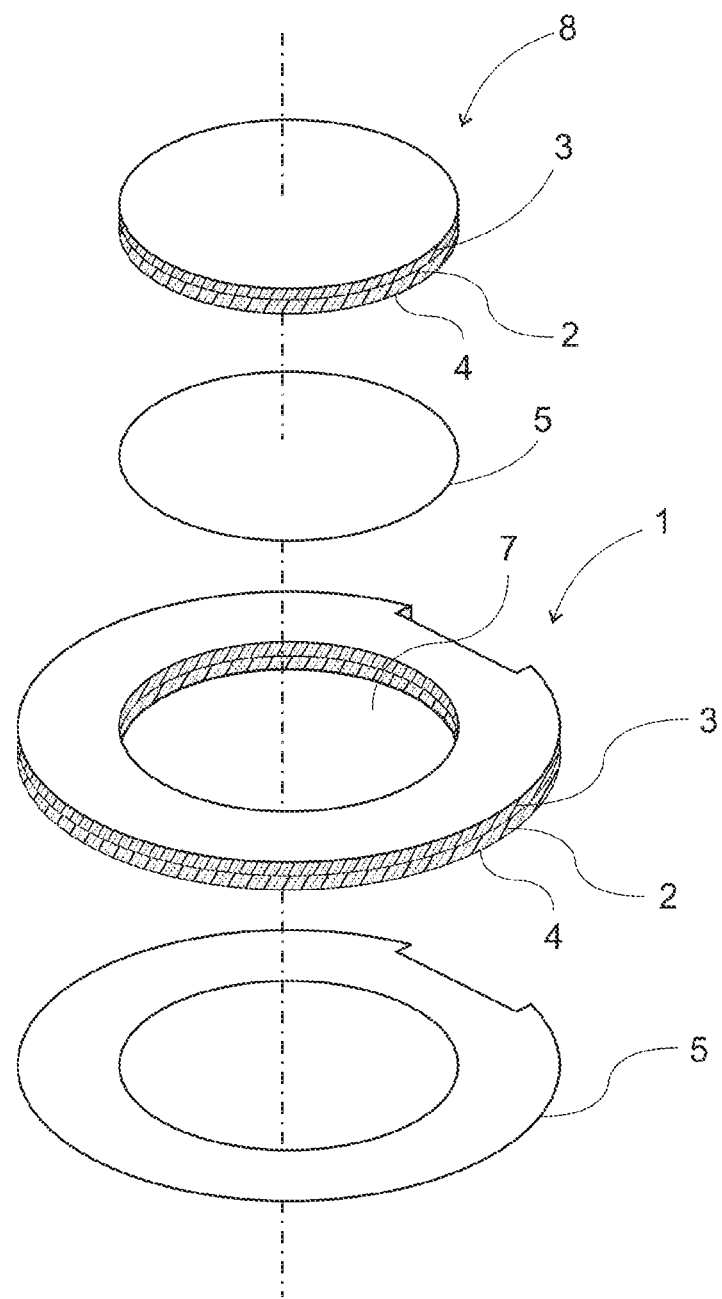
FIG. 2 is a top and side perspective view of a device according to the present invention.

The device 1 includes an adhesive layer 4 to attach the device with an ultrasound transducer or toco transducer. The adhesive layer 4 can be comprised of any low tack adhesive or attachment material known in the art that sufficiently attaches the device to the transducer while using an ultrasonic gel, yet allows for easy removal of the device 1 from the transducer without leaving a residue. As shown in FIG. 2, the device 1 can include a thin backing layer 5 that covers the adhesive layer 4. The backing layer 5 allows for easy storage of the device 1, by preventing the adhesive layer 4 of the device 1 from attaching with other objects when the device 1 is not in use. The backing layer 5 is peeled off to expose the adhesive layer 4 and attach the device 1 to the transducer prior to its use. Once the device 1 is attached with the transducer via the adhesive layer 4, the device 1 and transducer can be used externally on the woman's body such that the device 1 provides a comfortable layer of material between the transducer and woman's body. As shown in FIG. 1B, another embodiment of the device 1 can include at least one notch 6 located at its exterior edge 17 to fold device 1 over the outer edge of a transducer.

As illustrated in FIG. 2, the device 1 can be ring-shaped and comprised of a double-layer. The first layer 2 can be durable yet pliable. In this embodiment, the first layer 2 is attached with a transducer via an adhesive layer 4. The adhesive layer 4 can be attached with the bottom side of the first layer 2. Also shown in FIG. 2, a second layer 3 can be attached with the top side of the first layer 2. This second layer 3 is in contact with the patient, and thus can be formed of a softer material if desired.

A cutout portion 8 that is approximately the size of the aperture 7 of the device 1 is also shown in FIG. 2. This cutout portion 8 can also include an adhesive layer 4 so that it can be used on a transducer in conjunction with the device 1. As shown, the cutout portion 8 can also include the features of the device 1, such as a first layer 2, a second layer 3, and a removable backing layer 5.

As a non-limiting example, the device can be two inches in diameter and one-quarter inch thick, having a one-eighth inch thick first layer 2 of polyester material and a one-eighth inch thick second layer 3 of goggle foam. The device 1 can be used multiple times on the same patient.

When attached to a transducer, the device 1 lays flush with the surface of the transducer, providing a greater surface area of contact between the patient and the device compared to the contact surface area created between a patient and a transducer alone or a transducer that does not lay flush with the patient's body. Because the coefficient of friction created between the material of the device 1 and a patient's body is higher than that created between a smooth transducer and a patient's body, the device 1 maintains the transducers in place during monitoring.

When the device is used with ultrasonic gel, as transducers are regularly used with ultrasonic gel, the device 1 can hold the ultrasonic gel in place within its aperture 7. As a result, the device reduces any excess amount of gel on the patient's abdomen and the gel is not spread all over the patient's body. Thus, removal of the gel once monitoring is completed is easier for the practitioner. The device's adhesive layer 4 maintains its attachment with the transducer despite the device's contact with the gel. The device 1 also maintains its shape when used with the gel.

Figure 3A:
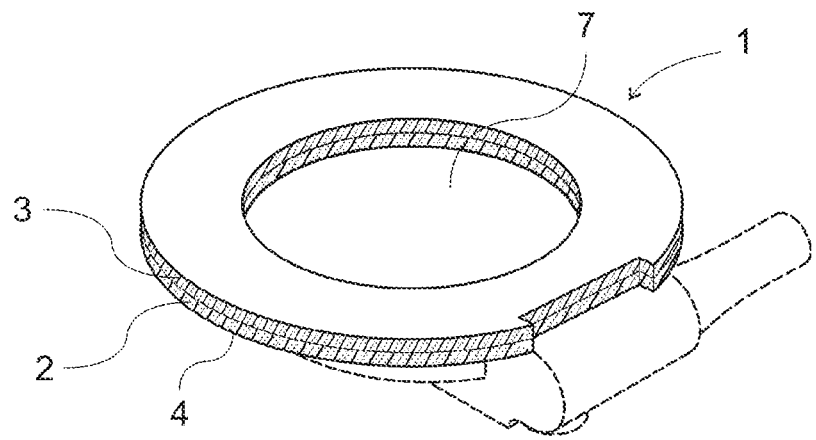
FIG. 3A is a top and side perspective view of a device according to the present invention attached with an ultrasound transducer.
Figure 3B:
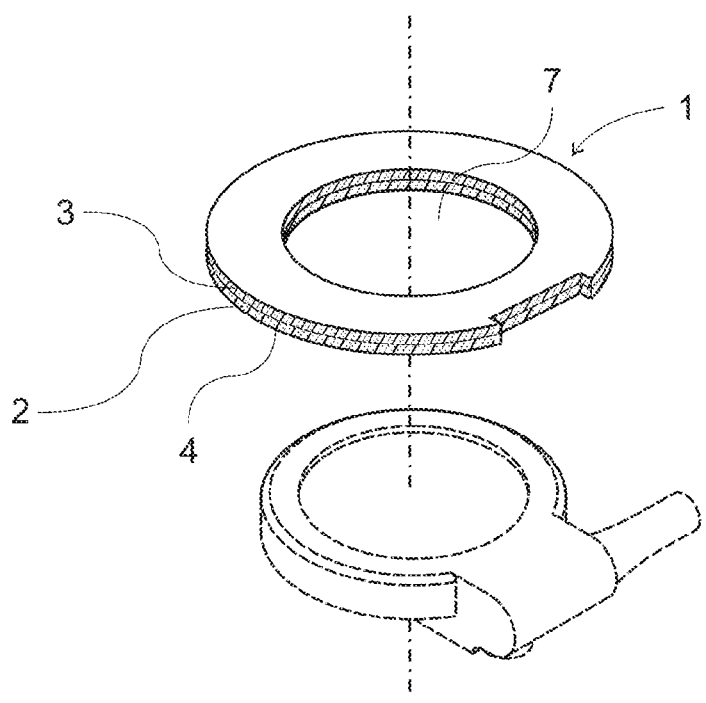
FIG. 3B is a top and side perspective view of a device according to the present invention unattached with an ultrasound transducer.

FIGS. 3A and 3B illustrate the device 1 attached and unattached with an ultrasound transducer, respectively. Ultrasound transducers are applied to a woman externally over the uterus to detect fetal heart tones. When the device 1 is attached with the transducer via the adhesive layer 4, the device 1 lays flush with the transducer to optimize the surface area of contact between the transducer and the patient. The device 1 can also include an aperture 7 through it to retain the ultrasonic gel and keep the transducer's detection of the fetal heart tones unobstructed.

The device 1 allows a more comfortable and pliable method for external fetal heart monitoring. When the device 1 is used during external fetal monitoring, the patient no longer suffers discomfort, so no adjustments of the transducer are needed. The transducer also stays in place with the use of the device 1 due to the higher coefficient of friction created between the device and woman's abdomen compared to the transducer alone. This results in a decreased amount of time spent on repositioning the ultrasound or toco transducers during labor. Consequently, the results of fetal external monitoring, which are continuous and printed out, or appear on a computer screen, are produced more comprehensively and without disruption when the device 1 is used, due to the fewer amount of adjustments. Overall, the device 1 allows the practitioner to trace the fetal heart rate with more ease and continuity than tracing the fetal heart rate without the device 1 attached to the transducer.

Figure 4A:
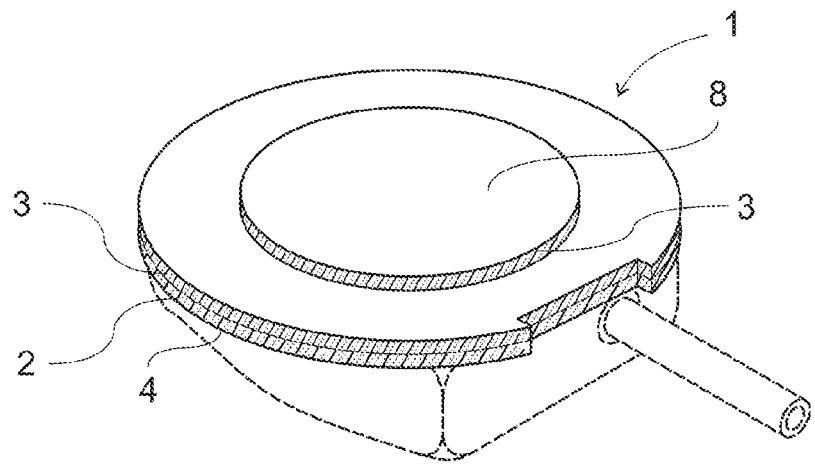
FIG. 4A is a top and side perspective view of a device according to the present invention attached with a toco transducer.
Figure 4B:
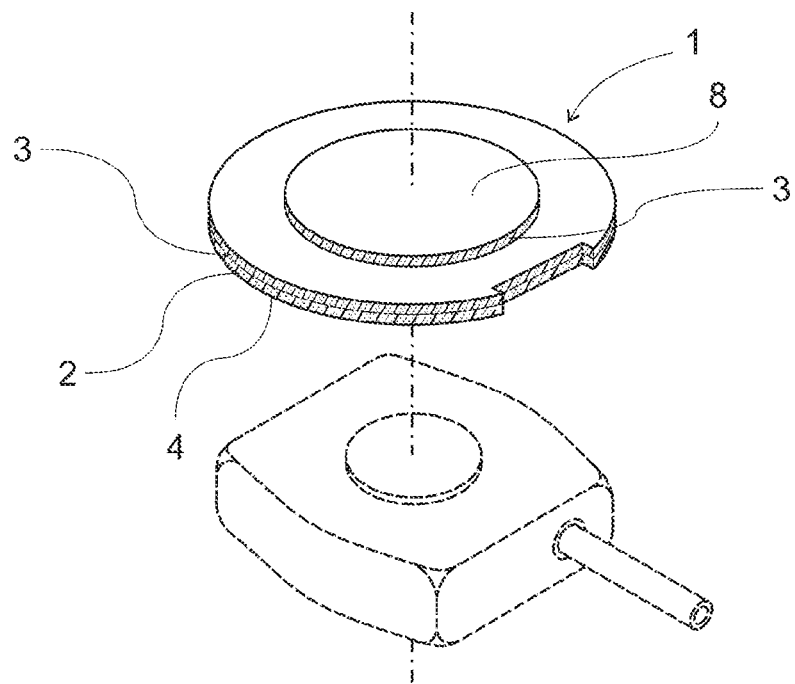
FIG. 4B is a top and side perspective view of a device according to the present invention unattached with a toco transducer.

FIGS. 4A and 4B illustrate the device 1 attached and unattached with a toco transducer, respectively. Toco transducers often include small round hard pressure gauges projecting out from the transducers. The toco transducers are placed externally on the top portion of the uterus to record uterine activity such as contractions with a pressure sensor. As shown in FIGS. 4A and 4B, the device 1 having an aperture 7 through its center can accommodate the round pressure gauge that projects from the toco transducer when the device 1 is attached to the toco transducer via the adhesive layer 4. In addition, a cutout portion 8 of the device 1, that can be formed when the aperture 7 is cut out of the device 1, can be attached with the projecting pressure gauge of the toco transducer to improve the comfort for the patient. The cutout portion 8 of the device 1 fits within the aperture 7 of the device 1 and can be made of the same materials as the device 1. The cutout portion 8 also includes an adhesive layer 4 for attachment with the pressure gauge of the toco transducer. Just as when used with the ultrasound transducer, when the device 1 is used with a toco transducer, the device 1 allows the practitioner to monitor the uterine activity with more ease than monitoring the uterine activity without the device 1 attached to the transducer.

Figure 5A:
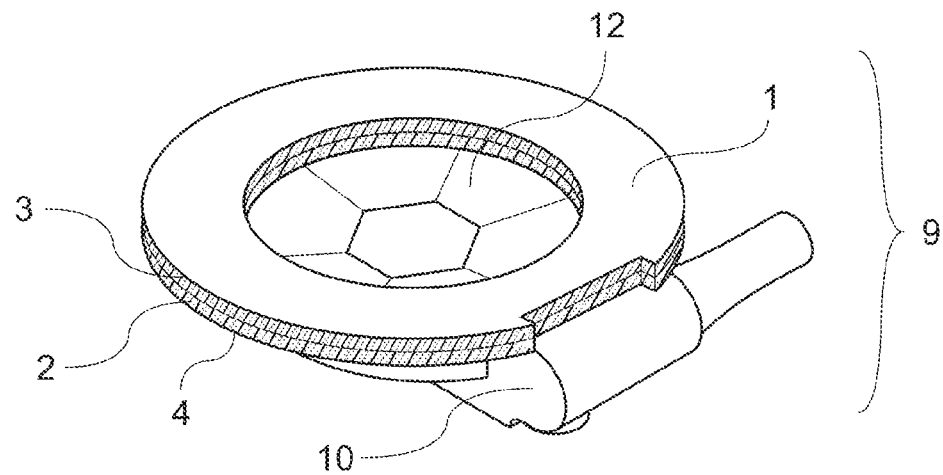
FIG. 5A is a top and side perspective view of an external monitoring system according to the present invention.
Figure 5B:
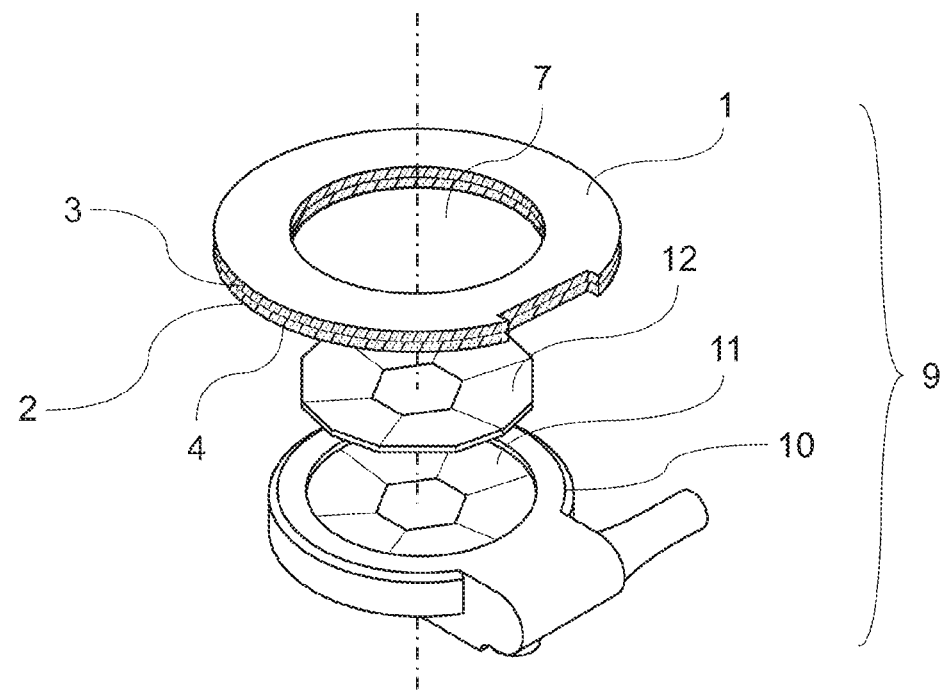
FIG. 5B is an exploded view of an external monitoring system according to the present invention.

The present invention also comprises an external fetal monitoring system 9, as shown in FIGS. 5A and 5B. In addition to the 1 device described herein, the external fetal monitoring system 9 includes a transducer 10. The transducer 10 has at least one sensor element 11 to detect fetal heart tones or intrauterine pressure, depending on the function of the transducer. The transducer also has an insulating layer 12 to shield the patient from electrical shock. In addition to the insulating layer 12, the device 1 creates an additional, separate, cushioning layer that is removably attached with the transducer 10 for added comfort and more continuous transducer readings.

The device 1 used in the system 9 has the same properties as the device 1 described herein. The device 1 includes an adhesive layer 4 to attach the device with the transducer 10 and can include a thin backing layer 5 that covers the adhesive layer 4 prior to its use. The device 1 can also include an aperture 7 through it to retain the ultrasonic gel and keep the transducer's detection of the fetal heart tones or intrauterine pressure unobstructed.

Importantly, when the device 1 is attached with the transducer 10, the device 1 lays flush with the patient to optimize the surface area of contact between the transducer 10 and the patient and to provide comfort to the patient. Further, the device 1 maintains the position of the transducer to improve the continuity of the transducer readings. For these reasons, the device is an improvement over transducers known in the prior art that often require adjustments to maintain their position and do not optimize the surface area contacting the patient nor provide comfort to the patient.

Figure 6:
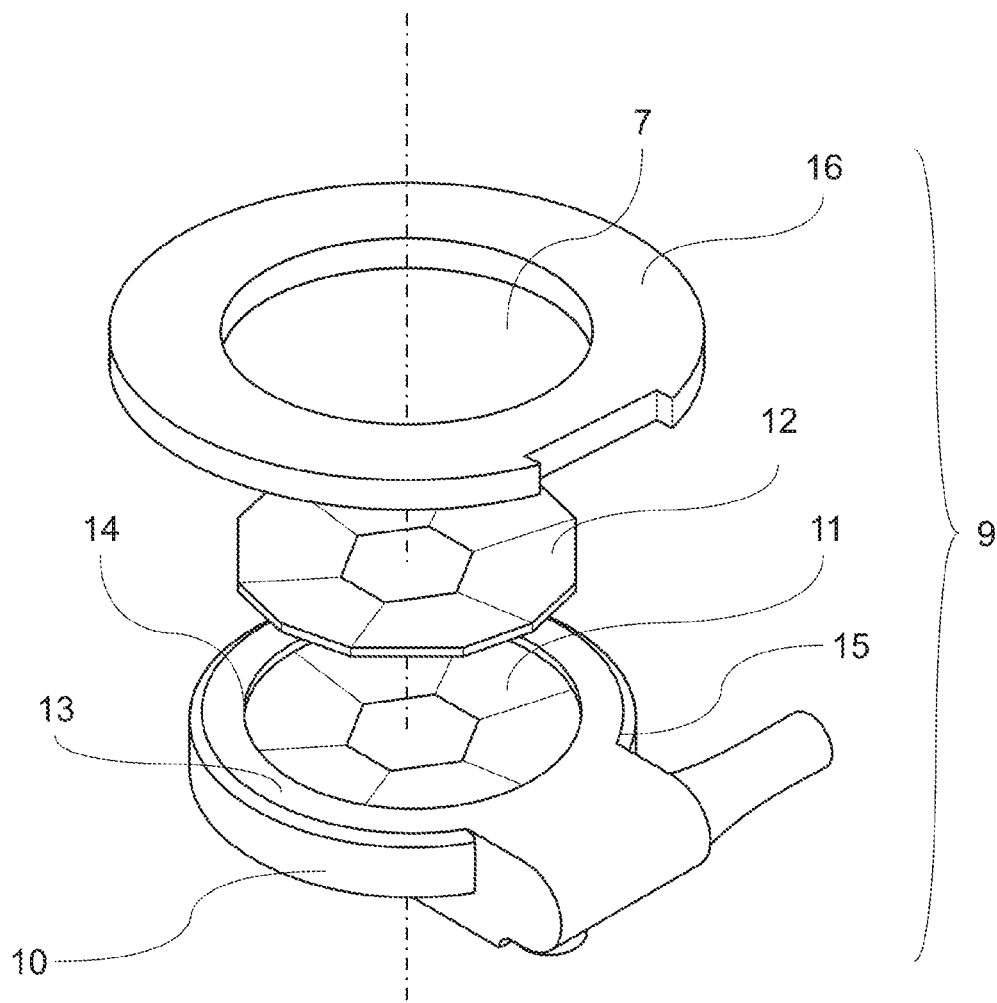
FIG. 6 is an exploded view of an external monitoring system according to the present invention.

As shown in FIG. 6, the external fetal monitoring system 9 can also be described as a system for use with a patient for monitoring a fetus. The system 9 includes a transducer which has a ring 13 having an interior circumference 14 and an exterior edge 15, at least one sensor element 11 to detect fetal heart rate or intrauterine pressure, and an insulating layer 12 shielding said patient from electrical shock located at least partially within the interior circumference 14 of the ring 13. The system 9 also includes at least one cushioning layer 16 distributed about said exterior edge 15 of said ring 13. The monitoring of the fetus is accomplished with greater continuity and greater comfort for a woman using the system 9 described herein.

While the foregoing describes the present invention in relation to illustrations and examples, it is understood that it is not intended to limit the scope of the invention to the illustrations and examples described herein. On the contrary, it is intended to cover all alternative modifications and equivalents that may be included in the spirit and the scope of the invention as defined by the appended claims.

I claim:

1. A device for contacting with a patient's skin for external fetal monitoring, the device comprising:
    an ultrasound transducer;
    a pad removably attached to said ultrasound transducer, said pad having a layer of a cushioning material, an adhesive layer, an aperture therethrough, and at least one recessed notch along an exterior edge of said layer of cushioning material, wherein said at least one recessed notch is spaced from said aperture;
    said layer of cushioning material having an outer surface for contacting with the patient's skin and an inner surface;
    said adhesive layer with a first surface and a second surface, said first surface attached to said inner surface of said layer of cushioning material, said second surface being removably attached only to said transducer, and said second surface and said outer surface are on opposite sides of said pad;
    said aperture defines a cavity for holding an ultrasonic gel; said cavity holds said gel in a larger amount compared to the amount that said transducer can hold without said pad attaching to said transducer; and
    wherein said device allows for continuous ultrasound transducer readings for fetal monitoring.

2. The device of claim 1, wherein said pad further comprises:
    a cutout portion comprised of said cushioning material, wherein said cutout portion is equal to or less than the size of said aperture; and a second adhesive layer attached with said cutout portion, wherein said second adhesive layer removably attaches with said transducer.

3. The device of claim 1, wherein said cushioning material is selected from the group consisting of a polyester, a polyether and a polyurethane material.

4. The device of claim 1, wherein said pad further comprises a backing layer removably attached to said second surface of said adhesive layer.

5. The device of claim 1, wherein said transducer comprises at least one sensor element and an insulating layer.

6. The device of claim 2, wherein said transducer comprises at least one sensor element and an insulating layer.

7. The device of claim 5, wherein said cushioning material is selected from the group consisting of a polyester, a polyether and a polyurethane material.

8. The device of claim 5, wherein said pad further comprises a backing layer removably attached with said second surface of said adhesive layer.

* * * * *